United States Patent
Kondo et al.

(10) Patent No.: US 9,075,006 B2
(45) Date of Patent: Jul. 7, 2015

(54) MEASUREMENT DEVICE AND FEATURE MEASUREMENT METHOD OF OBJECT TO BE MEASURED EMPLOYING SAME

(71) Applicant: MURATA MANUFACTURING CO., LTD., Nagaokakyo-Shi, Kyoto-fu (JP)

(72) Inventors: Takashi Kondo, Nagaokakyo (JP); Seiji Kamba, Nagaokakyo (JP)

(73) Assignee: MURATA MANUFACTRURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 14/199,043

(22) Filed: Mar. 6, 2014

(65) Prior Publication Data

US 2014/0252235 A1    Sep. 11, 2014

Related U.S. Application Data

(63) Continuation of application No. PCT/JP2012/060017, filed on Apr. 12, 2012.

(30) Foreign Application Priority Data

Sep. 6, 2011 (JP) .................. 2011-193885

(51) Int. Cl.
*G01J 5/02* (2006.01)
*G01N 21/51* (2006.01)
*G01N 21/25* (2006.01)
(Continued)

(52) U.S. Cl.
CPC .............. *G01N 21/51* (2013.01); *G01N 21/253* (2013.01); *G01N 21/3586* (2013.01); *G01N 21/03* (2013.01); *G01N 2021/0346* (2013.01); *G01N 21/3577* (2013.01); *B01L 3/50255* (2013.01); *G01N 2021/3595* (2013.01); *B01L 2300/0618* (2013.01)

(58) Field of Classification Search
CPC ..................... G01N 2021/651; G01N 21/3586
USPC ............................................ 250/341.1–341.8
See application file for complete search history.

(56) References Cited

U.S. PATENT DOCUMENTS

| 5,290,705 A | 3/1994 | Davis |
| 2003/0092075 A1 | 5/2003 | Pepper |

(Continued)

FOREIGN PATENT DOCUMENTS

| DE | 100 60 560 A1 | 12/2001 |
| EP | 1 486 767 A1 | 12/2004 |

(Continued)

OTHER PUBLICATIONS

Kelly et al., "An array of planar apertures for near-field fluorescence correlation spectroscopy," Apr. 2011, BioPhysical Journal, vol. 100, pp. L34-L36.*

(Continued)

*Primary Examiner* — Kiho Kim
(74) *Attorney, Agent, or Firm* — Arent Fox LLP

(57) ABSTRACT

A measurement device that includes a device main unit including at least one cavity for accommodating an analyte containing a specimen and an aperture array structure including a plurality of apertures extending therethrough in a direction perpendicular to a principal surface thereof. The aperture array structure is fixed such that part or all of the aperture array structure is positioned in the cavity.

15 Claims, 6 Drawing Sheets

(51) Int. Cl.
   *G01N 21/3586* (2014.01)
   *G01N 21/03* (2006.01)
   *B01L 3/00* (2006.01)
   *G01N 21/3577* (2014.01)
   *G01N 21/35* (2014.01)

(56) References Cited

U.S. PATENT DOCUMENTS

2007/0229094 A1   10/2007  Kasai et al.
2008/0165353 A1*  7/2008  Kataoka ........................ 356/246

FOREIGN PATENT DOCUMENTS

| EP | 1 930 714 A2 | 6/2008 |
|---|---|---|
| JP | 2007-010366 A | 1/2007 |
| JP | 2007-163170 A | 6/2007 |
| JP | 2008-083020 A | 4/2008 |
| JP | 2010-236868 A | 10/2010 |
| WO | WO 2004/007075 A2 | 1/2004 |
| WO | WO 2005-095929 A1 | 10/2005 |
| WO | WO-2011-070817 A1 | 6/2011 |

OTHER PUBLICATIONS

PCT/JP2012/060017 ISR dated May 9, 2012.
F. Miyamaru et al.; "Terahertz surface-wave resonant sensor with a metal hole array", Optics Letters, vol. 31, No. 8, Apr. 15, 2006, pp. 1118-1120.
Yoshida, Shigeki et al.; "A high-sensitivity terahertz sensing method using a metallic mesh with unique transmission properties", Journal of Molecular Spectroscopy, vol. 256, No. 1, May 3, 2009, pp. 146-151.

* cited by examiner

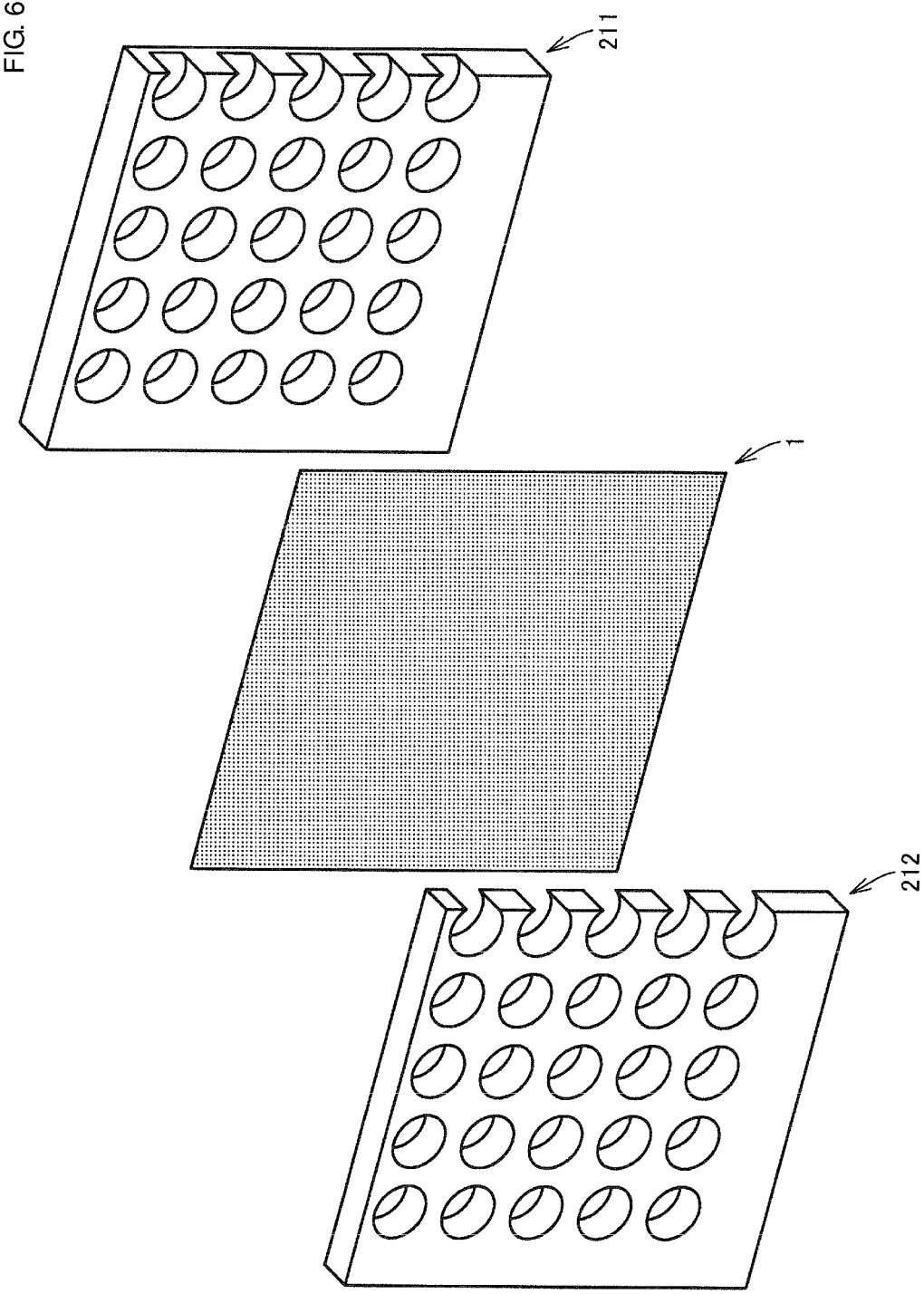

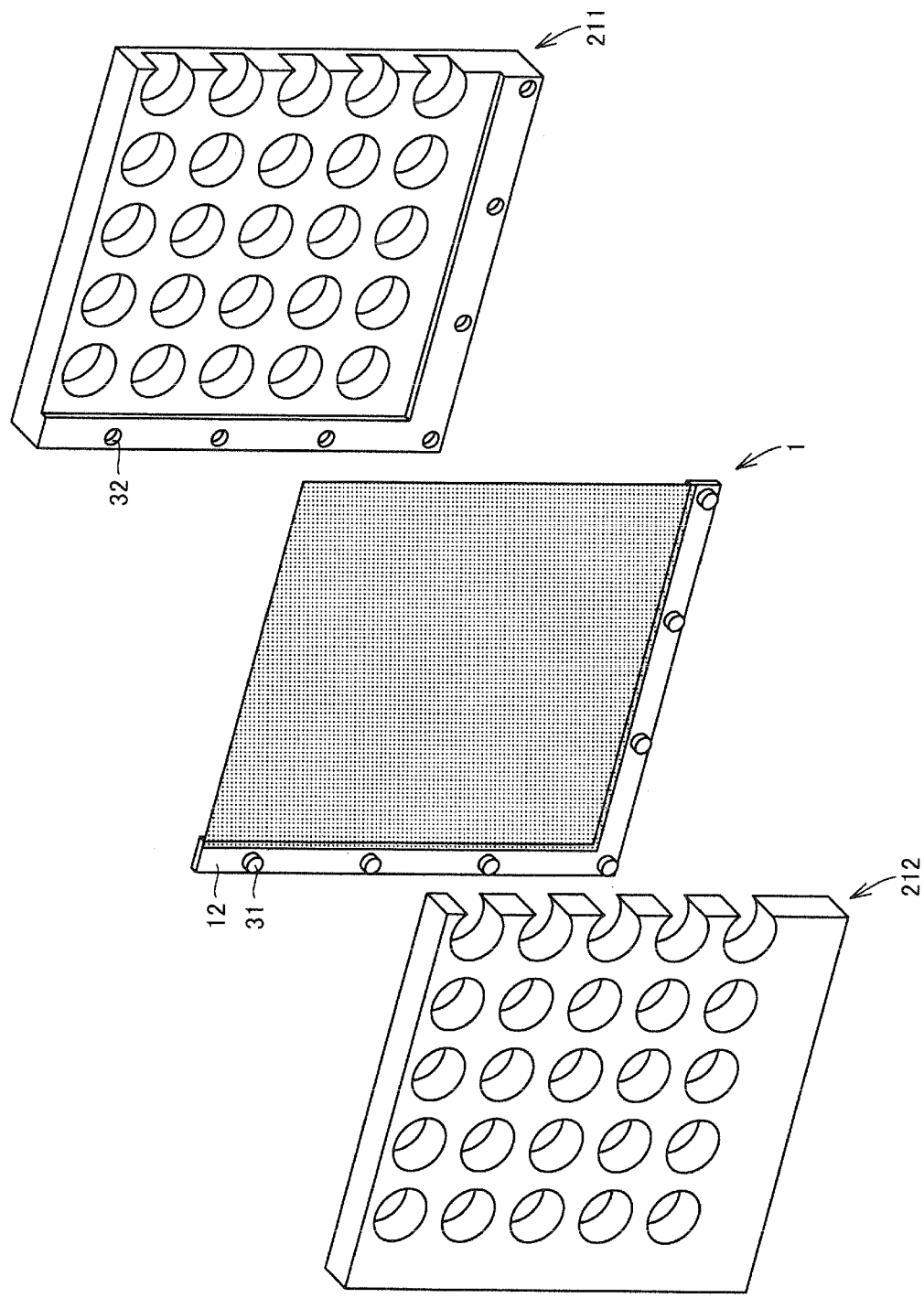

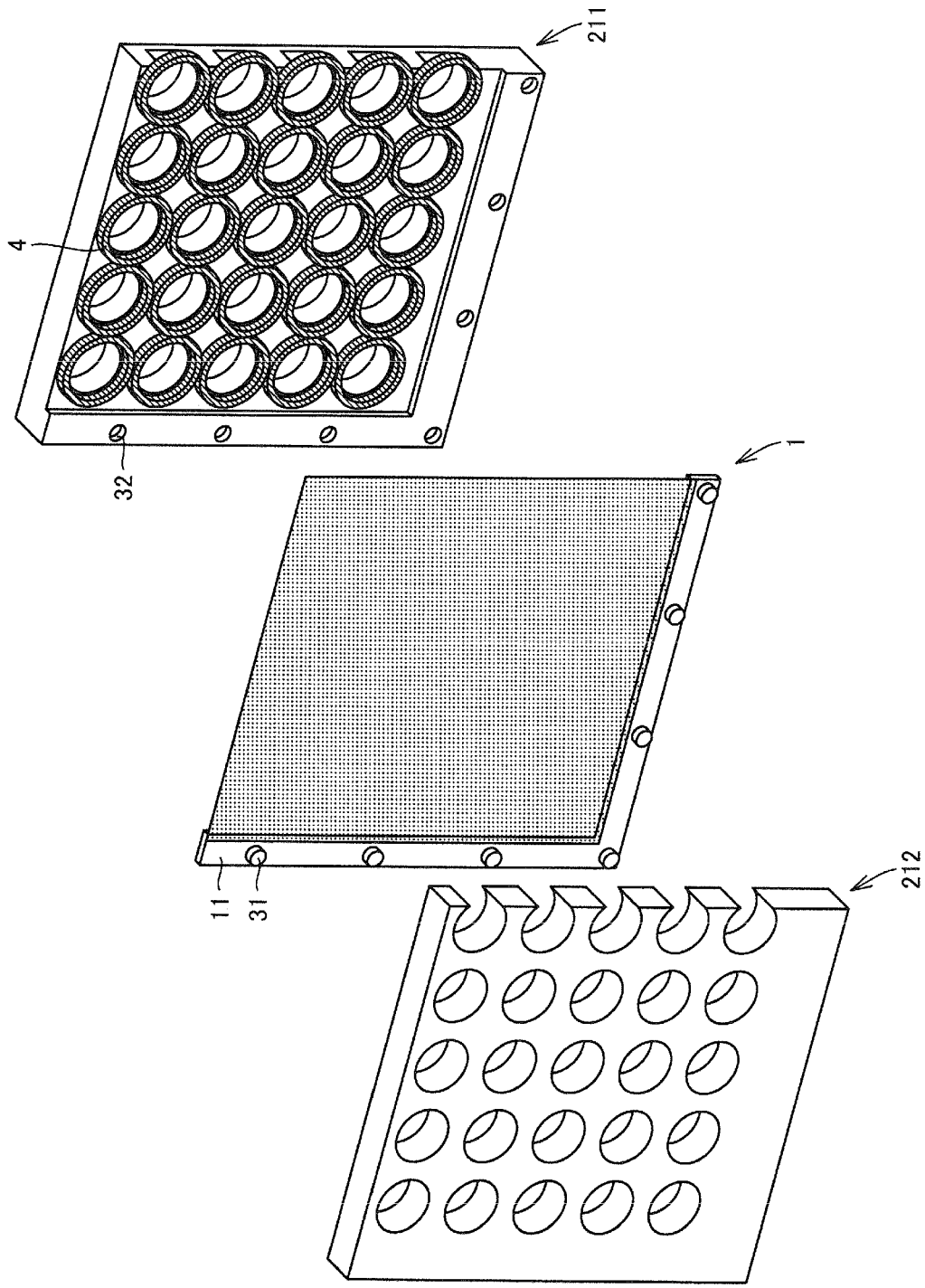

MEASUREMENT DEVICE AND FEATURE MEASUREMENT METHOD OF OBJECT TO BE MEASURED EMPLOYING SAME

CROSS REFERENCE TO RELATED APPLICATIONS

The present application is a continuation of International application No. PCT/JP2012/060017, filed Apr. 12, 2012, which claims priority to Japanese Patent Application No. 2011-193885, filed Sep. 6, 2011, the entire contents of each of which are incorporated herein by reference.

FIELD OF THE INVENTION

The present invention relates to a measurement device and a method of measuring characteristics of a specimen using the same.

BACKGROUND OF THE INVENTION

One example of a method for analyzing characteristics of a substance is to hold a specimen on an aperture array structure, radiate the aperture array structure on which the specimen is held with an electromagnetic wave, analyze a transmittance spectrum thereof, and measure the characteristics of the specimen. Specifically, for example, a technique of radiating a metal mesh filter to which a protein that is a specimen is attached with a terahertz wave and analyzing a transmittance spectrum thereof is used.

One example of a method of measuring a small amount of specimen with high sensitivity is to radiate an aperture array structure, such as a metal mesh, with an electromagnetic wave, such as a terahertz wave. For example, Patent Document 1 (Japanese Unexamined Patent Application Publication No. 2007-010366) discloses a method of holding an aperture array structure (e.g., metal mesh) including apertures and a specimen on a base closely adhering to the aperture array structure, radiating the aperture array structure with the specimen being held with an electromagnetic waves, detecting the electromagnetic wave passing through the aperture array structure, and thus measuring characteristics of the specimen on the basis of a change in frequency characteristic caused by the presence of the specimen.

Such a measurement method using the aperture array structure needs preprocessing, such as dropping an analyte on the aperture array structure, drying, and washing. However, it is preferred in, for example, a blood test in a medical institution that the measurement method involve no such preprocessing.

Patent Document 2 (Japanese Unexamined Patent Application Publication No. 2007-163170) discloses a method used when an analyte is liquid that contains a specimen (dissolved matter). The method is to measure characteristics of the specimen by radiating a container that accommodates both the liquid containing the specimen and an aperture array structure with an electromagnetic wave.

In the method described in Patent Document 2, the capacity of the container for accommodating the liquid and the aperture array structure is typically large, and the necessity of plenty of analyte (liquid) is a problem.

In addition, it is necessary for the method in Patent Document 2 that an electromagnetic wave, which serves as a probe, pass through two objects of the liquid including the specimen and the container. Typically, the liquid and the container reflect or absorb electromagnetic waves, and weakness of a signal of a transmitted electromagnetic wave and complication of analysis of obtained data are problems.

If the number of measurements or the number of kinds of specimens is large, the methods disclosed in Patent Documents 1 and 2 need tasks such as preparing a new aperture array structure and attaching a specimen for each measurement.

Examples of a factor for error relating to measurements can include dimensional variations in the aperture array structure. Such a factor for error has particularly a large influence if the amount of specimen is small and the change in frequency characteristic is very small. Dimensional variations in the aperture array structure increase in the order of in the same aperture array structure, among individuals of aperture array structures, and among production lots of aperture array structures.

Patent Document 1: Japanese Unexamined Patent Application Publication No. 2007-010366
Patent Document 2: Japanese Unexamined Patent Application Publication No. 2007-163170

SUMMARY OF THE INVENTION

The present invention is made to solve the above-described problems in the related art. It is an object of the present invention to provide a highly sensitive measurement device capable of measuring characteristics of a small amount of specimen without needing a large amount of analyte (liquid containing the specimen) and to provide a method of measuring characteristics of the specimen using the measurement device.

The present invention is a measurement device including a device main unit and an aperture array structure. The device main unit includes at least one cavity for accommodating an analyte containing a specimen. The aperture array structure includes a plurality of apertures extending therethrough in a direction perpendicular to a principal surface thereof. The aperture array structure is fixed such that part or all of the aperture array structure is positioned in the cavity.

The analyte may preferably be liquid. The aperture array structure may preferably be detachable from and attachable to the device main unit.

The at least one cavity included in the device main unit may preferably include a plurality of cavities arranged in an array. In that case, the aperture array structure may preferably be a single aperture array structure including a plurality of effective regions arranged in the plurality of cavities, respectively, and the aperture array structure may preferably be fixed to the device main unit such that the plurality of effective regions are positioned in the plurality of cavities, respectively.

The device main unit may preferably include a first member and a second member, and the aperture array structure may preferably be disposed between the first member and the second member. In that case, the aperture array structure may preferably include a frame member for holding the aperture array structure, and the frame member may preferably be disposed between the first member and the second member by engagement between the frame member and each of the first member and the second member. The device main unit may preferably include a magnetic material.

The measurement device may preferably be used for measuring characteristics of the specimen contained in the analyte by radiating the measurement device with an electromagnetic wave and detecting a frequency characteristic of the electromagnetic wave forward-scattered through or backscattered from the aperture array structure.

The present invention also relates to a method of measuring characteristics of a specimen using the measurement device. The method includes a first step of placing the analyte containing the specimen in the cavity, a second step of detaching the aperture array structure from the device main unit, and a third step of measuring the characteristics of the specimen contained in the analyte by radiating the aperture array structure with an electromagnetic wave and detecting a frequency characteristic of the electromagnetic wave forward-scattered through or backscattered from the aperture array structure.

According to the present invention, the capacity of the cavity for accommodating the analyte containing the specimen can be reduced, and highly sensitive measurement capable of measuring the characteristics of the specimen using a small amount of the analyte without needing a large amount of the analyte (liquid containing the specimen) can be achieved.

When the aperture array structure in the measurement device according to the present invention is detachable and attachable, the measurement can be conducted in a state where the aperture array structure is separated from the analyte and the container. Accordingly, highly sensitive measurement that is not affected by the analyte or the container can be achieved.

When the measurement device according to the present invention includes a plurality of cavities arranged in an array, even if the number of measurements or the number of kinds of specimens is large, because simultaneous work can be made, the time required for the work can be shortened, and throughput of the measurement can be improved. A process of cleaning the inside of the container for each of the kinds of specimens is not necessary, and biohazard can be reduced.

The use of a configuration in which portions of a single common aperture array structure are arranged in the plurality of cavities in the measurement device according to the present invention can reduce measurement errors resulting from dimensional variations among production lots of aperture array structures and those among individuals, and highly sensitive measurement can be achieved.

BRIEF DESCRIPTION OF THE DRAWINGS

FIG. 6 is an illustration for describing a method of producing the measurement device or a method of detaching an aperture array structure according to the second embodiment.

FIG. 7 is another illustration for describing the method of producing the measurement device or the method of detaching the aperture array structure according to the second embodiment.

FIG. 8 is still another illustration for describing the method of producing the measurement device or the method of detaching the aperture array structure according to the second embodiment.

DETAILED DESCRIPTION OF THE PREFERRED EMBODIMENTS

Figure 1:
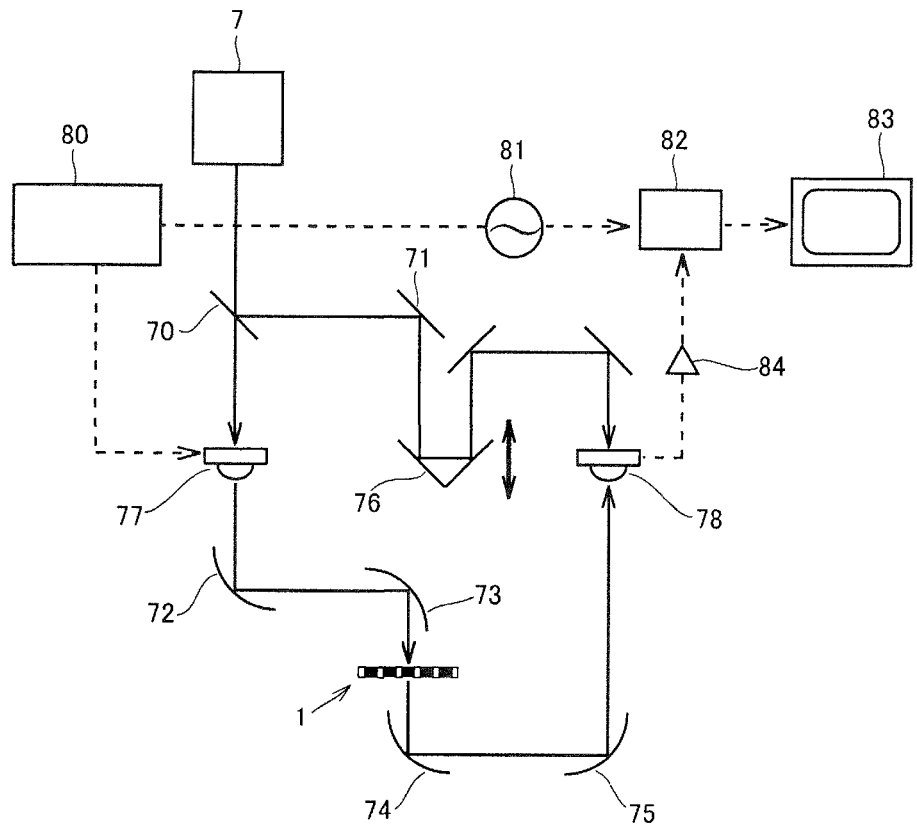
FIG. 1 is a schematic diagram for describing an outline of a measurement method according to the present invention.

First, an outline of one example of a measurement method according to the present invention is described with reference to FIG. 1. FIG. 1 schematically illustrates the entire structure of a measurement device used in the measurement method according to the present invention. The measurement device employs a pulse of an electromagnetic wave (e.g., a terahertz wave with a frequency of 20 GHz to 120 THz) generated by radiating a semiconductor material with a laser beam from a laser 7 (e.g., a short pulse laser).

In the configuration illustrated in FIG. 1, laser light emitted from the laser 7 is split into two paths by a semitransparent mirror 70. One of the laser beams is emitted to a photoconductive element 77 on the side where electromagnetic waves are generated, and the other is emitted to a photoconductive element 78 on the receiving side through a time-delay stage 76 using a plurality of mirrors 71 (including mirrors having the same function whose numerals are omitted). As each of the photoconductive elements 77 and 78, a typical element, such as one including a dipole antenna having a gap section in a low-temperature-grown gallium arsenide (LT-GaAs) portion, can be used. As the laser 7, a fiber laser or a solid-state laser, such as a titanium-sapphire laser, can be used. In generating and detecting an electromagnetic wave, a semiconductor surface can be used without the antenna or an electro-optic crystal, such as a zinc telluride (ZnTe) crystal, can be used. An appropriate bias voltage is applied to the gap section in the photoconductive element 77 on the generating side by a power source 80.

A generated electromagnetic wave is made into parallel beams by a parabolic mirror 72, and they are emitted to an aperture array structure 1 by a parabolic mirror 73. The aperture array structure 1 may be one that remains positioned in a cavity in a measurement device (microplate) described below or be one removed from the measurement device (microplate).

An electromagnetic wave that has passed through the aperture array structure 1 is received by the photoconductive element 78 by means of parabolic mirrors 74 and 75. An electromagnetic wave signal received by the photoconductive element 78 is amplified by an amplifier 84, and then the signal is obtained through a lock-in amplifier 82. The signal is subjected to signal processing, such as Fourier processing, in a personal computer (PC) 83 including calculation means, and then a transmittance spectrum for the flat aperture array structure 1 and the like are calculated. To obtain the signal by the use of the lock-in amplifier 82, a bias voltage to be applied from the power source 80 to the gap in the photoconductive element 77 on the generating side is modulated (with amplitude of 5 V to 30 V) using a signal of an oscillator 81. That performs synchronous detection and thus can improve the signal-to-noise ratio (S/N ratio).

The above-described measurement method is typically called terahertz time-domain spectroscopy (THz-TDS). Aside from THz-TDS, Fourier transform infrared spectroscopy (FT-IR) may also be used.

FIG. 1 illustrates a case where transmittance of an electromagnetic wave is measured. In the present invention, reflectance of an electromagnetic wave may also be measured. Preferably, transmittance in transmission in the zero-order direction or reflectance in reflection in zero-order direction may be measured.

Typically, a spectrum diffracted by a diffraction grating can be expressed by $$s(\sin i - \sin \theta) = n\lambda \tag{1}$$

where s indicates the grating spacing of the diffraction grating, i indicates the incident angle, θ indicates the diffraction angle, and λ indicates the wavelength. The zero-order in the "zero-order direction" described above indicates a case where n is zero in the above expression (1). Because s and λ are not zero, n is zero only when sin i−sin θ is zero. Accordingly, the "zero-order direction" described above indicates the direction in which the incident angle and the diffraction angle are the same, that is, the traveling direction of an electromagnetic wave does not change.

An electromagnetic wave used in the measurement method according to the present invention may preferably be an electromagnetic wave (terahertz wave) having a wavelength λ of 0.3 μm to 15 mm (frequency: 20 GHz to 1 PHz). For more highly sensitive measurement, the wavelength λ of an electromagnetic wave emitted to the aperture array structure may preferably be short and may preferably be equal to or smaller than 300 μm (frequency: 1 THz or more).

One specific example electromagnetic wave can be a terahertz wave emanating from a short pulse laser as a light source by the optical rectification effect of an electro-optic crystal, such as ZnTe. Another example can be a terahertz wave emanating from a short pulse laser as a light source by the instant occurrence of an electric current generated by exciting free electrons in a photoconductive antenna and applying a voltage to the photoconductive antenna. Still another example can be a terahertz wave emanating from a high-pressure mercury lamp or a high-temperature ceramic. Yet another specific example of the electromagnetic wave can be visible light emanating from a semiconductor laser or a photodiode.

An electromagnetic wave emitted to the aperture array structure in the measurement method according to the present invention may preferably be an electromagnetic wave of linearly polarized light. The electromagnetic wave of linearly polarized light may be one that is after an electromagnetic wave emanating from an unpolarized or circularly polarized light source passes through a (linear) polarizer or may be one of linearly polarized light emanating from a polarized light source. As the linearly polarizer, a wire grid may be used.

"Measurement of characteristics of a specimen" in the present invention is quantification or various types of qualitative analysis of a compound that is the specimen. Examples thereof can include measurement of the content of a very small quantity of the specimen in, for example, a solution and identification of the specimen. Specifically, an example is a method of soaking the aperture array structure in a solution in which the specimen is dissolved, attaching the specimen to the surface of the aperture array structure, then cleaning the solvent and a unnecessary component of the specimen, drying the aperture array structure, and then measuring characteristics of the specimen using a measurement device described below.

In the present invention, for determination of the amount of the specimen, it may preferably be calculated by measuring various quantities of the specimen in advance, finding their frequency characteristics, creating a calibration curve based on the frequency characteristics, and using comparison with the calibration curve.

<Measurement Device>

Next, the measurement device according to the present invention is described in detail. The measurement device according to the present invention includes a device main unit and an aperture array structure and features fixation of the aperture array structure such that part or all of the aperture array structure is positioned in a cavity.

(Device Main Unit)

The device main unit is a member that includes at least one cavity for accommodating an analyte containing a specimen. The analyte may preferably be liquid.

The device main unit may preferably be a member that includes a plurality of cavities arranged in an array, although it is allowed to be a container-shaped member including only one cavity. Such a device main unit including a plurality of cavities arranged in an array is typically called microplate. The microplate is a plate that includes a plurality of wells (cavities) and that has been used for measuring a specimen in an analyte, such as blood, in biochemical analysis, clinical laboratory examination, or the like. The measurement device according to the present invention features the aperture array structure being fixed such that part or all of the aperture array structure is positioned in a well or wells. When a microplate including many wells is used, a large amount of data is obtainable under the same condition, labor savings can be realized in the work, and high throughput at which a large number of samples and a larger amount of information can be processed at a time can be achieved.

In that case, the capacity of the well is typically on the order of from several microliters to several milliliters, and the amount of an analyte (liquid containing a specimen) can be reduced. In the case of the microplate, which is typically disposed of after use, a process of cleaning the inside of a container, is not necessary, unlike in the related art.

In that case, the measurement device according to the present invention may preferably include one aperture array structure including a plurality of effective regions arranged in a plurality of wells (cavities), and the aperture array structure may preferably be fixed to the device main unit such that the plurality of effective regions are positioned in the plurality of wells in the device main unit, respectively. That configuration can reduce measurement errors caused by dimensional variations in the aperture array structure, and highly sensitive measurement can be achieved.

The measurement device according to the present invention may preferably include fixing means for fixing a relative position between the device main unit and the aperture array structure. Furthermore, the fixing means may preferably be able to fix the aperture array structure to the device main unit such that the aperture array structure is detachable from and attachable to the device main unit. That configuration enables measurement to be conducted in a state where the aperture array structure is separated from an analyte and a container, and thus highly sensitive measurement that are not affected by the analyte or the container can be achieved. When the aperture array structure is detachable from and attachable to the device main unit, the aperture array structure can be easily collected to reuse metal (in particular, precious metal) included in the aperture array structure.

The measurement device according to the present invention may preferably be used for measuring characteristics of a specimen contained in an analyte by radiating the measurement device with an electromagnetic wave and detecting a frequency characteristic of the electromagnetic wave forward-scattered through or backscattered from the aperture array structure.

Examples of a material of the device main unit can include resin, such as polyethylene, polypropylene, polystyrene, and acrylic resin, glass, ceramic, and a semiconductor. A material that has small reflectance to a used electromagnetic wave and that less absorbs it may be preferable. The wells can have many shapes. For example, each of the wells may have a flat bottom or a round bottom, or the wells may be a combination of many long and narrow microtubes (deep well plate). Different shapes can be used, depending on the purpose of measurement.

(Aperture Array Structure)

The aperture array structure included in the measurement device according to the present invention includes a plurality of apertures extending therethrough in a direction perpendicular to its principal surface. Typically, its entire shape is flat or film-like.

The aperture array structure used in the present invention is a structure in which a plurality of apertures extending therethrough in a direction perpendicular to the principal surface are arranged periodically in at least one direction. One such example can be a structure in which a plurality of apertures are arranged in a matrix in the direction of the principal surface of the aperture array structure. Not all of the apertures may be periodically arranged. It is merely necessary to periodically arrange at least part of the apertures.

The aperture array structure may preferably be a quasi-periodic structure or a periodic structure. The quasi-periodic structure is a structure that does not have translational symmetry but maintains order. Examples of the quasi-periodic structure can include a Fibonacci structure as a one-dimensional quasi-periodic structure and a Penrose structure as a two-dimensional quasi-periodic structure. The periodic structure is a structure that has spatial symmetry, typified by translational symmetry, and can be classified into a one-dimensional periodic structure, a two-dimensional periodic structure, and a three-dimensional periodic structure, depending on the dimension(s) of the symmetry. Examples of the one-dimensional periodic structure can include a wire-grid structure and a one-dimensional diffraction grating. Examples of the two-dimensional periodic structure can include a mesh filter and a two-dimensional diffraction grating. Of those periodic structures, the two-dimensional periodic structure may preferably be used. More preferably, the periodic structure in which apertures are regularly arranged vertically and laterally (in a rectangular array).

Figure 2:
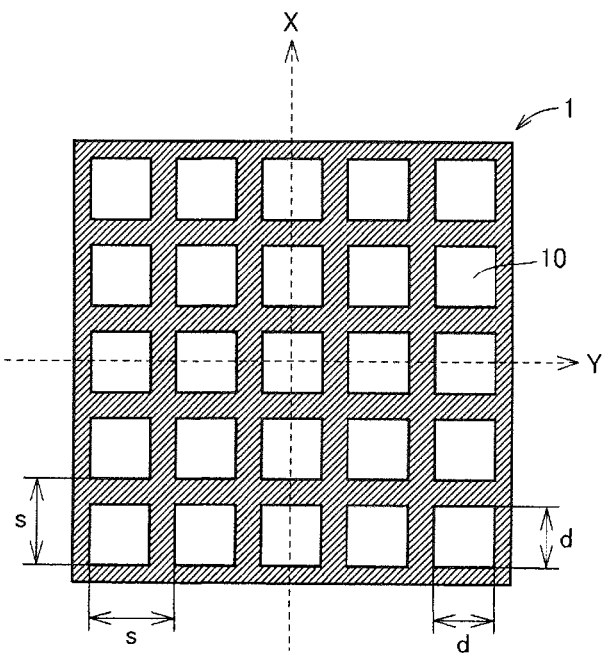
FIG. 2 is a front view of an example of an aperture array structure used in the present invention.

One example of the two-dimensional periodic structure with apertures in a rectangular array can be a plate structure (grating structure) illustrated in FIG. 2, in which apertures 10 are arranged at constant intervals in a matrix. The aperture array structure 1 illustrated in FIG. 2 is a plate structure in which the apertures 10 each having a square shape as seen from the direction of its principal surface are spaced at the same intervals in two arrangement directions perpendicular to the sides of the square (vertically and laterally in FIG. 2). The shape of each of the apertures is not limited to the square. Other examples of the shape may be a rectangle, a circle, and an oblong. The shape of the aperture is not limited to the above-described examples having symmetry. Other example of the shape may be a shape in which a part of the aperture has a protrusion or a cut portion. If the apertures are arranged in a square array, the spacings in the two arrangement directions may be different. For example, a rectangular array may also be used.

The thickness (t) of the aperture array structure may preferably be equal to or smaller than a fraction of the wavelength $\lambda$ of an electromagnetic wave used in measurement. For example, when the wavelength $\lambda$ of an electromagnetic wave used in radiation is 300 µm, t may preferably be equal to or smaller than 150 µm. If the thickness of the structure exceeds that range, the strength of the transmitted or reflected electromagnetic wave may be weak, and it may be difficult to detect a signal.

The size of the aperture (e.g., d in FIG. 2) in the aperture array structure may preferably be equal to or larger than one-tenth of the wavelength $\lambda$ of an electromagnetic wave used in measurement and equal to or smaller than 10 times the wavelength $\lambda$. If the size of the aperture is out of that range, the strength of the transmitted electromagnetic wave may be weak, and it may be difficult to detect a signal.

The grating spacing (pitch) of the aperture (e.g., in FIG. 2) may preferably be equal to or larger than one-tenth of the wavelength $\lambda$ of an electromagnetic wave used in measurement and equal to or smaller than 10 times the wavelength $\lambda$. If the grating spacing of the aperture is out of that range, the electromagnetic wave may be hard to pass.

The shape and dimensions of the aperture array structure and the aperture are designed depending on the measurement method, the material characteristic of the aperture array structure, the frequency of the used electromagnetic wave, and the like. It is difficult to generalize the ranges thereof, and the ranges are not limited to the above-described examples.

The aperture array structure may preferably be made of a metal. Example of the metal can include a metal that can be bound to a functional group, such as a hydroxyl group, thiol group, or carboxyl group, included in a compound, a metal that allows the surface to be coated with a functional group, such as a hydroxyl group or an amino group, and an alloy of the above-described metals. Specifically, examples of the metal can include gold, silver, copper, iron, nickel, titanium, chromium, silicon, and germanium. Preferably, the metal may be gold, silver, copper, nickel, titanium, or chromium. More preferably, the metal may be nickel or gold.

The use of gold or nickel is effective in particular when a specimen includes a thiol group (—SH group) because the thiol group can be bound to the surface of the aperture array structure. The use of nickel is effective in particular when a specimen includes a hydroxyl group (—OH) or a carboxyl group (—COOH) because that functional group can be bound to the surface of the aperture array structure.

The aperture array structure can be fabricated by various publicly known methods but may preferably be made by patterning on the surface of a plate or film support base. The patterning may be performed by a typical process of forming an electrode on a semiconductor (e.g., resist application, pattern printing, resist pattern formation, metal deposition, resist removal) or the like.

<Method of Measuring Characteristics of Specimen>

The method of measuring characteristics of a specimen according to the present invention includes a first step, a second step, and a third step described below. The above-described measurement device is used in the measurement method.

First Step

At the first step, an analyte containing a specimen is placed in a cavity in the measurement device. The specimen in the analyte placed in the cavity in the measurement device is typically held on the aperture array structure (effective region positioned in the cavity in the measurement device).

Various publicly known methods can be used in holding a specimen on the aperture array structure. For example, the specimen may be attached directly to the aperture array structure or may be attached thereto with a support film disposed therebetween or the like. In terms of conducting measurement with reproducibility enhanced by improvement in measurement sensitivity and reduction in variations in measurement, the specimen may preferably be attached directly to the surface of the aperture array structure.

The cases where the specimen is attached directly to the aperture array structure includes not only a case where a chemical bond or the like is directly formed between the surface of the aperture array structure and the specimen but also a case where the specimen is bound to a host molecule attached in advance to the surface of the aperture array structure. Examples of the chemical bond can include a covalent bond (e.g., a covalent bond between a metal and a thiol group) a Van der Waals bond, an ionic bond, a metallic bond, and a hydrogen bond. Preferably, the covalent bond may be used. The host molecule is a molecule to which the specimen can be specifically bound. Example of a combination of the host molecule and the specimen can include an antigen and a antibody, a sugar chain and a protein, a lipid and a protein, a low-molecular compound (ligand) and a protein, a protein and a protein, and a single-stranded DNA and a single-stranded DNA.

Second Step

At this step, the aperture array structure is detached from the device main unit. Before detaching the aperture array structure from the device main unit, typically, it is necessary to release the fixing means for fixing the aperture array structure to the device main unit. In some cases, for example, if the device main unit including a first member and a second member and the aperture array structure are magnetically fastened together, the aperture array structure being fixed can be manually separated from the device main unit with ease.

Third Step

At this step, the aperture array structure detached at the second step is radiated with an electromagnetic wave, the frequency characteristic of the electromagnetic wave forward-scattered through or backscattered from the aperture array structure is detected, and thereby measuring the characteristics of the specimen contained in the analyte.

In the measurement method according to the present invention, the characteristics of the specimen are measured on the basis of at least one parameter relating to the frequency characteristic of the scattered electromagnetic wave in the above-described aperture array structure. For example, the characteristics of the specimen can be measured on the basis of a change in a dip waveform occurring in the frequency characteristic of the electromagnetic wave forward-scattered (passing) through the aperture array structure or a peak waveform occurring in the frequency characteristic of the electromagnetic wave backscattered (reflected) therefrom, the change being caused by the presence of the specimen.

The dip waveform is a waveform in a valley portion (convex downward) that partially appears in the frequency characteristic (e.g., transmittance spectrum) for the flat periodical structure in a frequency range where the ratio of a detected electromagnetic wave to an electromagnetic wave used in radiation (e.g., transmittance of the electromagnetic wave) relatively increases. The peak waveform is a mountain shaped (upward convex) waveform that partially appears in the frequency characteristic (e.g., reflectance spectrum) for the flat periodical structure in a frequency range where the ratio of a detected electromagnetic wave to an electromagnetic wave used in radiation (e.g., reflectance of the electromagnetic wave).

The present invention is described in further detail below with reference to specific embodiments, to which the present invention is not limited.

First Embodiment

Figure 3:
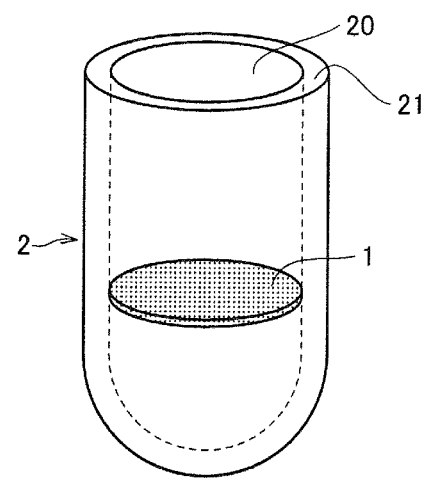
FIG. 3 is a schematic diagram that illustrates one configuration of a measurement device according to a first embodiment.

FIG. 3 is a schematic diagram that illustrates one configuration of the measurement device according to a first embodiment. As illustrated in FIG. 3, the aperture array structure 1 (or part thereof) is arranged in a cavity (well) 20 in a measurement device 2 according to the present embodiment.

The aperture array structure 1 may preferably be detachable from and attachable to a device main unit 21 including the cavity 20. In that case, measurement can be conducted in a state where the aperture array structure is separated from the analyte or the container, and thus highly sensitive measurement that is not affected by the analyte or the container can be achieved.

The material of the device main unit (container) 21 may preferably less absorb a used electromagnetic wave. The material of the device main unit (container) 21 may preferably have a small reflectance to the used electromagnetic wave. In those cases, the effects on measurement caused by the device main unit can be reduced, and the measurement can be highly sensitive.

Figure 4:
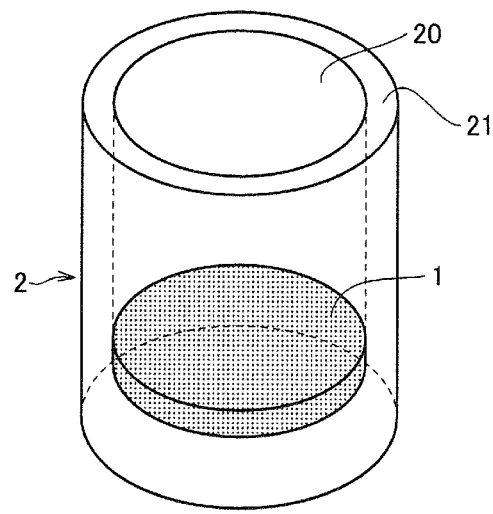
FIG. 4 is a schematic diagram that illustrates another configuration of the measurement device according to the first embodiment.

In FIG. 3, the aperture array structure 1 is arranged in an intermediate position in the cavity 20. The aperture array structure 1 may be arranged on the bottom portion of the cavity 20, as illustrated in FIG. 4.

To measure characteristics of a specimen, liquid containing the specimen is inserted into the cavity 20 in the container 2, and the specimen is attached to the aperture array structure 1 by appropriate processing, such as allowing to stand or agitation. Then, the aperture array structure 1 is detached from the measurement device 2, then the aperture array structure 1 is radiated with an electromagnetic wave, and the characteristics of the specimen are measured from the transmission characteristics of the electromagnetic wave or the like. In that way, the separation of the aperture array structure 1 from the analyte and the container enables highly sensitive measurement.

It may be preferable that a redundant dissolved matter attached to the aperture array structure 1 be removed before measurement conducted by radiating the aperture array structure 1 with an electromagnetic wave. If a cleaning process for cleaning a deposition on the aperture array structure 1 other than the specimen is needed, when the cleaning process is performed after detachment of the aperture array structure 1, some work, such as dispensing cleaning liquid, can be omitted, unlike in a case where the inside of the container is cleaned, and the cleaning can be easier.

Second Embodiment

Figure 5:
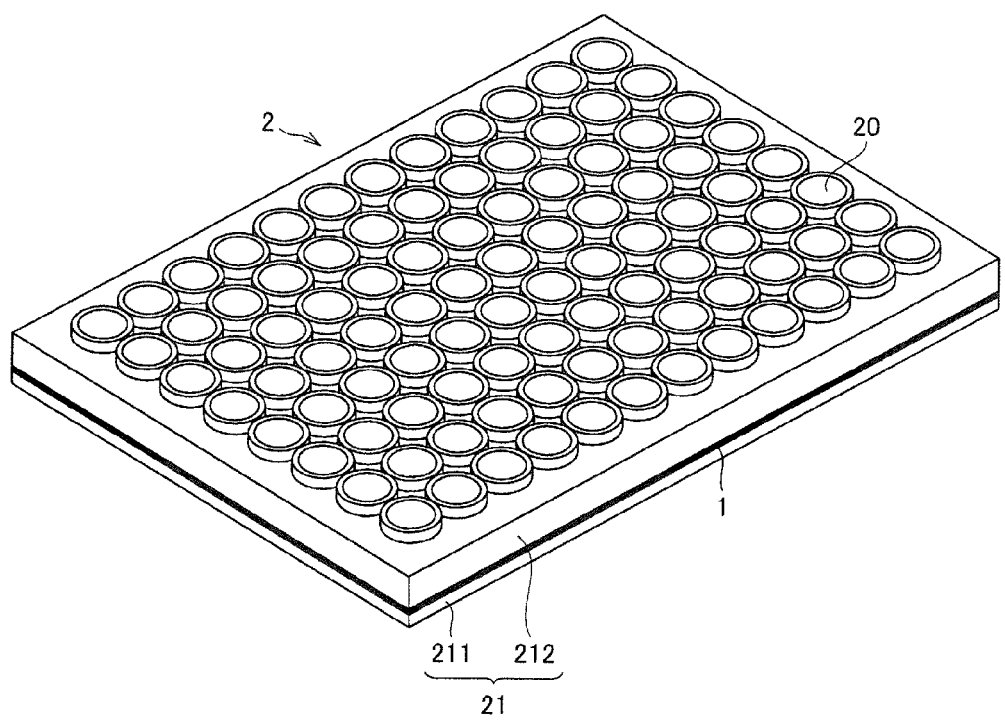
FIG. 5 is a perspective view that illustrates a measurement device according to a second embodiment.

FIG. 5 is a perspective view of the measurement device according to a second embodiment. As illustrated in FIG. 5, in the present embodiment, the device main unit 21 includes a plurality of cavities 20 for accommodating liquid containing a specimen, and the cavities 20 are arranged in an array. That configuration enables high-throughput measurement capable of processing a large number of samples and a larger amount of information at a time.

In FIG. 5, the aperture array structure 1 is disposed between a first member (well bottom component) 211 forming the bottom section of the cavities (wells) 20 and a second member (well upper component) 212 forming the upper section of the wells 20 and is arranged such that the effective regions of the aperture array structure 1 are positioned inside the wells 20. The aperture array structure 1 may be spaced away from the bottom of each of the wells 20, as illustrated in FIG. 3, or may be in contact with the bottom of each of the wells 20, as illustrated in FIG. 4. The aperture array structure 1 may preferably be spaced way from the bottom of each of the wells 20. In addition, the distance between the aperture array structure 1 and each of the wells 20 may preferably be substantially equal to or more than the distance from the principal surface of the aperture array structure 1 in a range where an electromagnetic field is enhanced in the aperture array structure 1.

That is because the bottom of each of the wells 20 is not included in the range where the electromagnetic field is enhanced in the aperture array structure 1 and thus the measurement sensitivity is improved.

In the present embodiment, the effective region of the aperture array structure 1 positioned in each of the wells 20 is part of the aperture array structure 1 of the same individual. Thus dimensional variations in the effective region are smaller than dimensional variations among individuals of aperture array structures and those among production lots of aperture array structures. Accordingly, measurement errors caused by dimensional variations can be reduced, and highly sensitive measurement can be achieved.

(Method of Producing Measurement Device and Method of Detaching Aperture Array Structure)

FIGS. 6, 7, and 8 are illustrations for describing a method of producing the measurement device or a method of detaching the aperture array structure according to the present embodiment.

FIG. 6 is an exploded view of the measurement device (microplate) in which the aperture array structure 1 is disposed between the first member (well bottom component) 211 and the second member (well upper component) 212.

The first member (well bottom component) 211 and the second member (well upper component) 212 may preferably include a magnetic substance. That is because the aperture array structure 1, which includes a metal material, can be easily fastened, and the aperture array structure 1 is detached from the microplate main unit (first member 211 and second member 212). Separation of the aperture array structure 1 from liquid (analyte) containing a specimen and the container (device main unit) in measurement enables highly sensitive measurement and array scanning measurement that are not affected by the analyte or the container.

In FIG. 7, with the aim of facilitating detachment of the aperture array structure 1, the aperture array structure 1 is provided with a frame member (support) 12. Male members (protrusions) 31 on both sides of the frame member 12 (in FIG. 7, only one side is illustrated) and female members (cavities) 32 on the side near the aperture array structure 1 in each of the first member 211 and the second member 212 (in FIG. 7, only the female members in the first member 211 are illustrated) are engaged with each other, thereby fixing the aperture array structure 1 in a predetermined position between the first member 211 and the second member 212. Even if engagement means as the fixing means is included, as described above, the first member 211 and the second member 212 may include a magnetic substance.

In FIG. 8, with the aim of preventing liquid leakage (osmosis) among wells, a rubber ring 4 is disposed on the periphery of each of the wells on the side near the aperture array structure 1 of each of the first member 211 and the second member 212 (in FIG. 8, only the rings 4 on the first member 211 are illustrated). The above-described well structure and the structure including the rings 4 can prevent contamination among the wells.

As equipment used in measurement employing the measurement device (microplate) according to the present embodiment, a microplate reader for detecting and measuring absorbance, fluorescence, and emission is particularly important. That enables a large number of samples in minute quantities at a time. In addition, a centrifuge for use in a microplate and a device that automatically inserts and extracts samples and performs cleaning can also be used.

REFERENCE SIGNS LIST

1 aperture array structure, 10 aperture, 12 frame member, 2 measurement device (microplate), 20 cavity, 21 device main unit (microplate main unit), 211 first member, 212 second member, 31 male member (protrusion), 32 female member (cavity), 4 ring, 7 laser, semitransparent mirror, 71 mirror, 72, 73, 74, 75 parabolic mirrors, 76 time-delay stage, 77, 78 photoconductive elements, 80 power source, 81 oscillator, lock-in amplifier, 83 personal computer (PC), 84 amplifier.

The invention claimed is:

1. A measurement device comprising:
   a device main unit including at least one cavity constructed to accommodate an analyte containing a specimen;
   a first member and a second member;
   an aperture array structure disposed between the first member and the second member, the aperture array structure including a plurality of apertures extending therethrough in a direction perpendicular to a principal surface thereof,
   wherein the aperture array structure is fixed such that part or all of the aperture array structure is positioned in the cavity.

2. The measurement device according to claim 1, wherein the analyte is liquid.

3. The measurement device according to claim 1, wherein the aperture array structure is detachable from and attachable to the device main unit.

4. The measurement device according to claim 3, wherein the measurement device is configured such that the aperture array structure is separated from the analyte or the container during measurement.

5. The measurement device according to claim 1, wherein the measurement device is configured such that the aperture array structure is separated from the analyte or the container during measurement.

6. The measurement device according to claim 1, wherein the at least one cavity included in the device main unit comprises a plurality of cavities arranged in an array.

7. The measurement device according to claim 6, wherein the aperture array structure is a single aperture array structure including a plurality of effective regions arranged in the plurality of cavities, respectively, and
   the aperture array structure is fixed to the device main unit such that the plurality of effective regions are positioned in the plurality of cavities, respectively.

8. The measurement device according to claim 1, wherein the aperture array structure includes a frame member constructed to hold the aperture array structure, and
   the frame member is disposed between the first member and the second member by engagement between the frame member and each of the first member and the second member.

9. The measurement device according to claim 1, wherein the device main unit includes a magnetic substance.

10. The measurement device according to claim 1, wherein the measurement device measures characteristics of the specimen contained in the analyte by radiating the measurement device with an electromagnetic wave and detecting a frequency characteristic of the electromagnetic wave forward-scattered through or backscattered from the aperture array structure.

11. The measurement device according to claim 1, wherein the first member is a well bottom component and the second member is a well top component.

12. The measurement device according to claim 11, wherein the well bottom component and the well top component collectively form the at least one cavity.

13. A method of measuring characteristics of a specimen using a measurement device, the method comprising:

placing an analyte containing the specimen in at least one cavity of a main unit of the measurement device, wherein part or all of an aperture array structure, which includes a plurality of apertures extending therethrough in as direction perpendicular to a principal surface thereof, is positioned in the at least one cavity;

detaching the aperture array structure from the main unit of the measurement device; and measuring the characteristics of the specimen contained in the analyte by radiating the aperture array structure with an electromagnetic wave and detecting a frequency characteristic of the electromagnetic wave forward-scattered through or backscattered from the aperture array structure.

14. The method of measuring characteristics of a specimen according to claim 13, wherein the analyte is liquid.

15. The method of measuring characteristics of a specimen according to claim 13, wherein measurement is conducted in a state where the aperture array structure is separated from the analyte or the container.

\* \* \* \* \*